United States Patent [19]

Silberman

[11] Patent Number: 5,096,285
[45] Date of Patent: Mar. 17, 1992

[54] MULTIFOCAL MULTIZONE DIFFRACTIVE OPHTHALMIC LENSES

[75] Inventor: Donn M. Silberman, Corona Del Mar, Calif.

[73] Assignee: Iolab Corporation, Claremont, Calif.

[21] Appl. No.: 523,146

[22] Filed: May 14, 1990

[51] Int. Cl.⁵ .......................... G02C 7/04; A61F 2/16
[52] U.S. Cl. .................................... 351/161; 623/6
[58] Field of Search ............... 351/160 R, 160 H, 161, 351/162; 623/6

[56] References Cited

U.S. PATENT DOCUMENTS

| | | | |
|---|---|---|---|
| 4,162,122 | 7/1979 | Cohen | 351/161 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,636,211 | 1/1987 | Nielsen et al. | 623/6 |
| 4,637,697 | 1/1987 | Freeman | 351/161 |
| 4,642,112 | 2/1987 | Freeman | 623/6 |
| 4,813,955 | 3/1989 | Achatz et al. | 623/6 |
| 4,881,804 | 11/1989 | Cohen | 351/161 |
| 4,923,296 | 5/1990 | Erickson | 351/161 |

Primary Examiner—Scott J. Sugarman

[57] ABSTRACT

Multifocal lenses for improving vision are disclosed. The lenses of the present invention use at least one diffractive zone located in a defined portion of the surface of a refractive lens to achieve highly efficient multifocal vision by providing nearly 100% efficiency in the +1 diffractive order. The lenses disclosed may be used for both contact lenses and intraocular lens as well as other vision correcting applications.

4 Claims, 4 Drawing Sheets

MULTIFOCAL MULTIZONE DIFFRACTIVE OPHTHALMIC LENSES

The present invention relates to multifocal lenses for correcting vision and, more specifically relates to bifocal lenses having at least one diffractive zone which is added to the basic refractive power of the lens.

BACKGROUND OF THE INVENTION

Ophthalmic lenses which have two or more distinct focal lengths are known. Such lenses have been used in the post as contact lenses which are disposed upon the surface of the eye, or as intraocular lenses (IOL's) which are surgically implanted to replace the natural crystalline lens after its removal during, e.g., cataract surgery. Diffractive lenses are well known within the field of optics generally, however they have as yet found only limited application to intraocular or contact lens design. Thus, although numerous designs have been disclosed for multifocal optics for use in contact or intraocular lenses, few have been found to be in any way practical.

Lenses relying solely upon refraction have been disclosed. For example, Nielsen, et al. U.S. Pat. No. 4,636,211 discloses a bifocal intraocular lens which has achieved by refraction, the central zone adapted for near vision and surrounded by a coaxial far vision zone. The lenses disclosed have either a plano-convex or bi-convex shape. Achatz et al. U.S. Pat. No. 4,813,955 discloses a multifocal intraocular artificial ophthalmic lens divided into near range and far range zones disposed symmetrically about the lens axis which uses the refractive power of the lens material and its shape to achieve bi-focal vision.

Designs of contact lenses which rely only upon the refractive properties of the Fresnel lens are also known. For example, Cohen U.S. Pat. No. 4,162,122 discloses a zonal bifocal contact lens comprised of a concave spherical or aspherical posterior surface and a continuous anterior surface which is divided into concentric annular rings which are alternately inclined to the optical axis, corresponding to curvatures appropriate for the near and distant foci. The interfaces of the annular zones are continuous and do not create any steps or jumps on the anterior surface. Each zone consists of a refractive element only, the zones forming a smooth anterior surface.

Lenses utilizing the combined properties of Fresnel lenses and Fresnel zone plates and which rely on the diffractive effects thereof are also known. Cohen U.S. Pat. No. 4,210,391 discloses multifocal optical lenses which have their multifocal properties distributed throughout the lens. The lenses disclosed share the incident light between the focal points by using a zone plate and splitting the incident light into discrete "bundles" each directed to a particular focal point. The design utilizes elements of both a Fresnel lens and a Fresnel zone plate, relying on the fact that such optical elements are comprised of concentric rings or zones and thus provides lens designs having reduced diffractive and chromatic aberrations. Cohen U.S. Pat. No. 4,338,005 also discloses a multifocal phase plate lens design which has multifocal properties distributed throughout the lens. The lens disclosed is comprised of concentric zones, the diameters of which are derived from the focal length desired and wavelength of light being focused. The performance of the lens is not degraded by the superposition of blurred images at the focal points. Also, Cohen U.S. Pat. No. 4,340,283 discloses a multifocal zone plate construction suitable for use in optical systems with multifocal requirements. A phase shift multifocal zone plate provides multiple foci by adjusting the zone plate spacings such that the zone plate foci coincide with multifocal Fresnel lens foci. The adjustment is obtained by ion implantation in certain sections of the lens, whereby the refractive index of the lens is altered in that section.

Additionally, others have attempted to combine both refractive and diffractive powers to create multifocal lenses. Freeman U.S. Pat. No. 4,673,697 discloses multifocal contact lenses utilizing diffraction and refraction by adding diffractive power to the basic refractive power of the lens. The diffractive power is provided by a series of concentric zones defined by surface discontinuities or refractive index changes. In a bifocal application, diffractive power is provided in addition to the basic refractive power of the lens, while maintaining the basic curvature of the front and rear surfaces. The diffractive zones deviate all of the incident light in the manner of a phase zone plate (Fresnel zone plate). The Freeman U.S. Pat. No. 4,673,697 teaches that it is important to maintain the radius of curvature of the rear surface of the lens at a value which will maintain close conformance with the cornea. Freeman U.S. Pat. No. 4,642,112 discloses bifocal artificial eye lenses which utilize a transmission holograms to provide diffractive power on a wavelength or amplitude selective basis in a manner which is additive to the basic refractive power of the lens.

When a diffraction element is used to provide two separate focal lengths, the maximum theoretical efficiency results in about 40.5% of the incident light forming an image at each focal distance. Therefore, the overall total efficiency of the lens is about 81%. The remainder of the light (about 19%) is scattered into higher order diffraction patterns and thus degrades the images formed, rather than enhancing them. Therefore, it would be desireable to provide multifocal lenses which utilize both diffractive and refractive elements and which exhibit an overall total efficiency closer to an ideal 100%.

SUMMARY OF THE INVENTION

It is therefore an object of the present invention to provide a highly efficient multifocal lens. Accordingly, the present invention provides increased efficiency multifocal lenses by using at least one diffractive zone located in a defined portion of the surface of a refractive lens. The lenses of a first embodiment of the present invention are thus divided into two areas, a first area of highly efficient diffractive power and a second area having essentially no diffractive power. Most preferably, the diffraction zones provide substantially 100% efficiency in the +1 diffractive order. The non-diffractive zones allow light to be transmitted without appreciable deviation due to diffraction. Most preferably, the zones are of about equal area, thereby causing about one-half of the incident light to focus at each of the two focal planes, resulting in an overall lens efficiency approaching 100%.

In another preferred embodiment, lenses are provided which have two different diffractive elements disposed substantially across the entire lens surface. The two diffractive patterns are different in that they have different diffractive powers. Since the diffractive powers are additive to a basic lens power provided by the lens upon which the diffractive elements are disposed, a multifocal lens having adequate power and high efficiency is achieved. For example, highly efficient zones having diffractive powers of about 10 diopters and 14 diopters can be provided for distance and near vision respectively. These diffractive powers are additive to the refractive basic power of the lens upon which they are disposed, e.g., a 10 diopter biconvex lens. Thus, in this example, 20 diopters of optic power are provided for distance vision and 24 diopters are provided for near vision. Since the diffractive zones are preferably high efficiency diffractive elements, a bifocal lens is provided which approaches 100% efficiency.

DETAILED DESCRIPTION OF THE PREFERRED EMBODIMENTS

The present invention presents numerous advantages over the prior designs discussed above. Primarily, the present invention increases the overall aggregate efficiency of the lens. Ideally, 50% of the incident light is provided to the focal point. One image is created from distant objects and one image is created from near objects. The increased efficiency of the lenses of the present invention provide the maximum possible image contrast and resolution. Preferably the high efficiency diffraction zone has an optical efficiency of the greatest practical value, i.e., about 98%. In a preferred embodiment, a high efficiency diffraction grating is produced. Since about 98% of the light that passes through the diffractive zones will be focused on the retina for near objects and substantially all of the light that passes through the refractive zones will be focused on the retina for distant objects, improved multifocal vision is achieved. The present invention therefore overcomes the problem of unwanted light scattering caused by higher diffractive orders. Thus, lenses of the present invention have a higher potential efficiency than any known prior art design.

Figure 1:
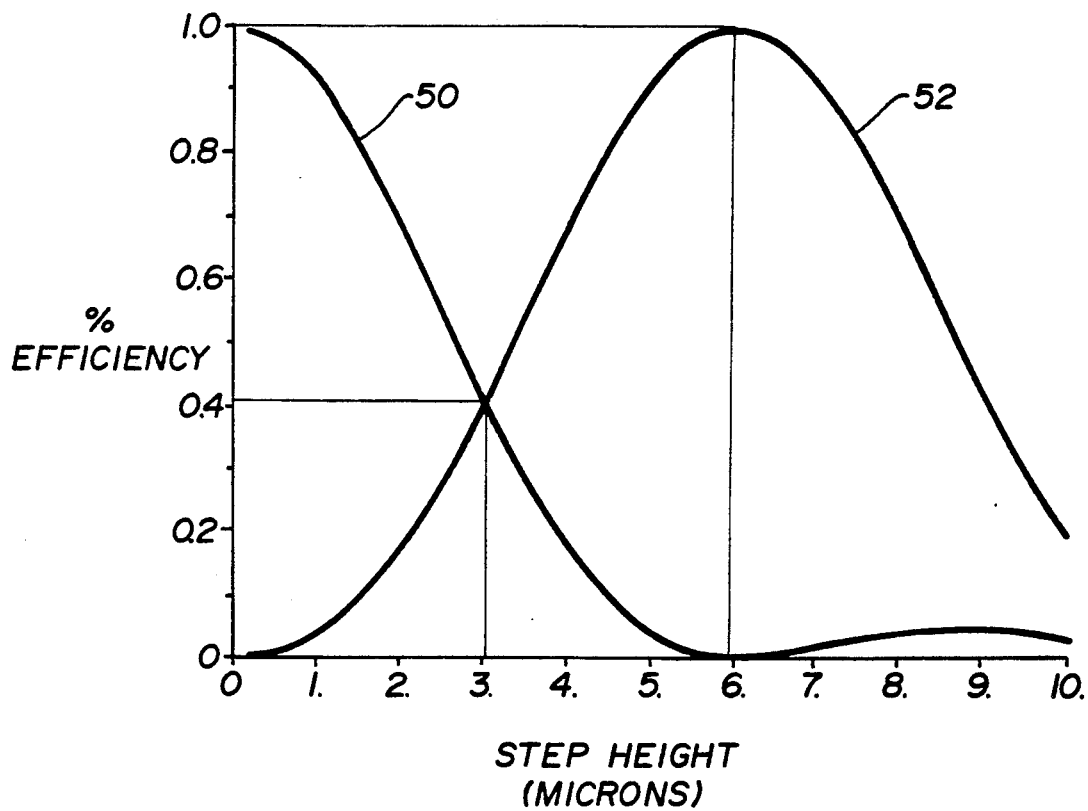
FIG. 1 is a graph of the optical efficiency of a diffractive lens element.

As set forth above, the maximum theoretical efficiency available from a standard phase zone plate is about 81%. The intermittent diffractive/non-diffractive construction of the present invention has the potential to exhibit considerably higher efficiencies. The efficiency, of a diffractive lens element, as a percentage of transmitted light, is shown graphically in FIG. 1. The efficiency is plotted against the step height, in microns, on the lens surface for a silicone lens in water. A first plot line 50 depicts the efficiency of the 0th (zeroth) order diffraction. A second plot line 52 depicts the efficiency of the 1st (first) order diffraction. In the typical prior art lenses discussed above, a step height equivalent to slightly more than 3 microns was chosen to evenly divide the first and zero order diffraction gradients, thereby causing about 40% of the light to be focused at a near focal length and about 40% of the light to be focused at a far focal length. The overall efficiency is thus about 80%. However, in the lenses of the present invention, a step height of about 6 microns is chosen. As clearly seen in FIG. 1, at this step height, almost 100% of the incident light is refracted at the first order. Thus, almost 100% of the light can be focused at either the near or the far focal length. By providing alternating 100% efficiency sectors, some focused for near and some for far, a nearly 100% efficient lens is achieved.

Figure 2:
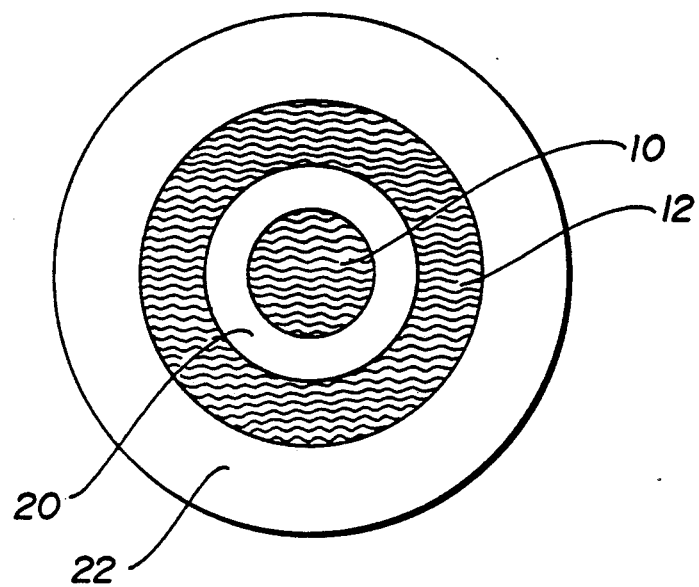
FIG. 2 is a plan view of a preferred embodiment of a lens made in accordance with the present invention which has two diffractive elements divided into an annular and a circular zone.

A plan view of an embodiment of a lens made in accordance with the present invention is depicted in FIG. 2. The lens may either be utilized in a contact lens or in an intraocular lens, therefore, unrelated features such as the haptics used to secure an intraocular lens in the eye are not shown. Bifocal vision is preferably achieved by providing a lens, such as a biconvex diffractive lens, which has a basic power and creating high efficiency diffractive zones 10,12 which provide additive diffractive power to the basic lens power. It will be understood that the term "additive power" refers to the arithmetic addition of the power of the lens elements, therefore, in some embodiments, the diffractive power may be negative and reduce the overall power of that zone.

As shown, n one preferred arrangement it is desirable to place a circular diffractive zone 10 at approximately the center axis of the lens and dispose a second diffractive zone 12 in an annular spaced relationship with the first. Lying between the diffractive zones 10,12 are refractive zones 20,22, which possess the basic lens power only. Therefore, a portion of the incident light will fall upon the refractive zones 20,22 and provide focus at a first focal length. The optical efficiency of this zone will be the same as the optical efficiency of the basic lens, and if made to the highest commercial standards, will approach 100%. Another portion of the incident light will fall upon the diffractive zones 10,12 and also pass through the basic lens. Thus, the power of this portion of the lens will be the additive sum of the diffractive and refractive powers and will provide focus at a second focal length. The highest commercially available techniques for imparting a diffractive element are utilized to create the diffractive zones, 10,12, thereby providing about 98% efficiency. As a result, the performance of the overall lens approaches 100% efficiency.

In a typical intraocular lens application, lenses such as that depicted in FIG. 2 will have an overall diameter of about 7.0 millimeters (mm). Most preferably, the innermost diffractive zone 10 will have a diameter of about 1.72 mm, the first refractive zone 20 will have an outside diameter of about 2.90 mm, the next diffractive zone will have an outside diameter of about 4.60 mm and the second refractive zone will have an outside diameter of about 7.00 mm. As will be understood by those of ordinary skill, the design dimensions may be varied somewhat to achieve particular corrective effects. It will also be understood that the order of placement of the diffractive and refractive zones may be reversed, i.e., the central zone may be refractive, etc.

Figure 3:
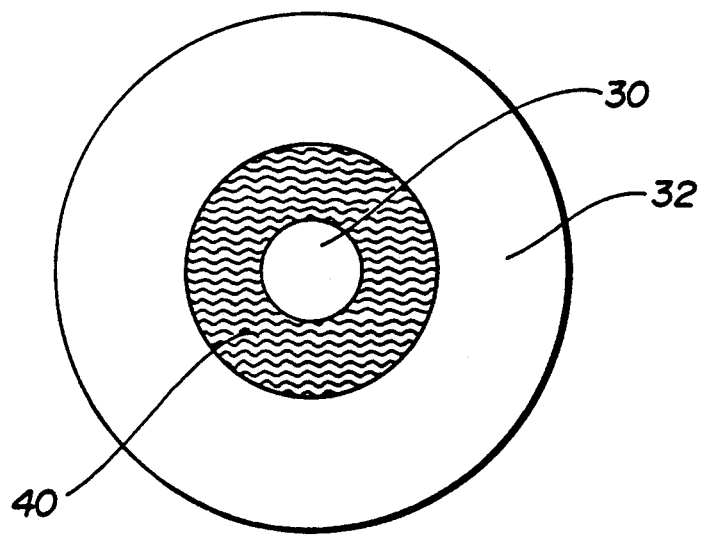
FIG. 3 is a plan view of another preferred embodiment of a lens made in accordance with the present invention which has a single diffractive element comprised of an annular zone.

Another embodiment of a lens having similar properties to that shown in FIG. 2 is depicted in FIG. 3. The lens design shown has a centrally disposed first refractive zone 30, preferably of about 1.3 mm diameter if used in a 7.00 mm intraocular lens. Surrounding the first refractive zone 30 is a diffractive zone 40, which preferably has an outer diameter of about 3.36 mm. A second refractive zone 32 surrounds the refractive zone 40 and has an outer diameter of about 7.00 mm. As set forth above, in certain embodiments it may be desirable to alter the dimensions given or to reverse the arrangement of the zones.

Figure 4:
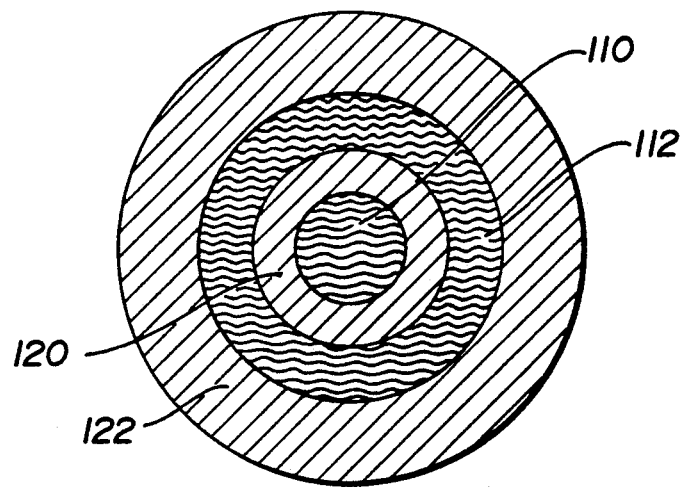
FIG. 4 is a plan view of a preferred embodiment of the present invention which has two diffractive elements each divided into two zones.

Referring now to FIG. 4, an embodiment of a high efficiency lens utilizing both diffractive and refractive elements over its entire surface to achieve bifocal vision is shown. The lens depicted in FIG. 4 has two zones of a first diffractive power 110,112 for distance vision and two zones of a second diffractive power 120,122 for near vision. Although the layout of the zones shown places the zones in a series of annular rings, it should be understood that numerous other layouts are comprehended by the present invention. Also, as demonstrated with reference to FIGS. 2-3, the number of zones may be expanded or reduced. In this embodiment of the present invention, two zones of different diffractive powers are placed in an additive manner relative to a lens having a basic power to achieve multiple focal points. As will be readily understood by those of ordinary skill, the layout, shape and relative size of the zones is dependent upon the specific correction required.

In a preferred embodiment of the lens depicted in FIG. 4, a lens preferably provides a basic refractive power of about 10 diopters, achieved using a bi-convex lens or other lens designs known to those of ordinary skill. An additional 10 diopters of a first diffractive power is added by two diffractive zones 110,112, thereby providing a total power of 20 diopters for distance vision. Two near vision diffractive zones 120,122 which have a second diffractive power of about 14 diopters are also provided, resulting in a total near vision power of 24 diopters.

Figure 5:
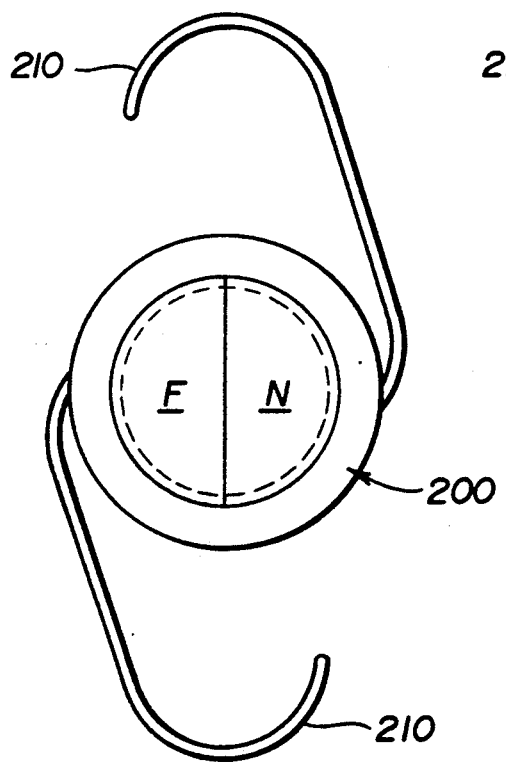
FIG. 5 is a plan view of an intraocular lens made in accordance with the present invention which has a far vision zone and a near vision zone defined by bisecting the lens.
Figure 6:
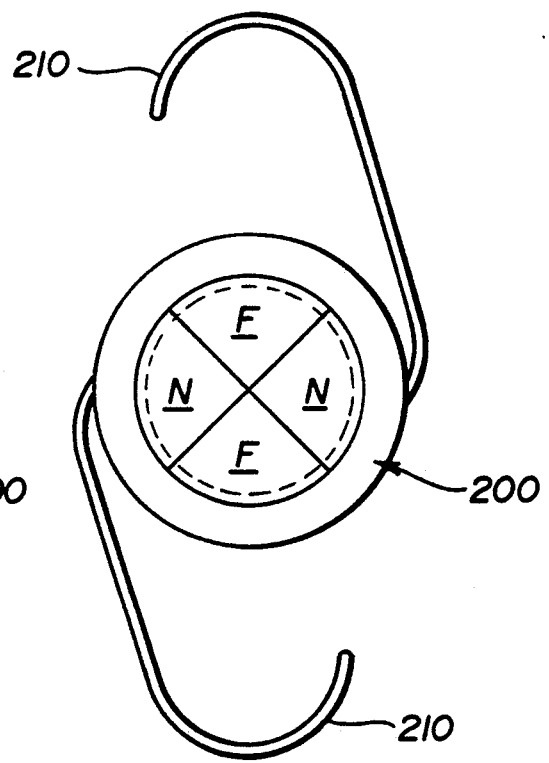
FIG. 6 is a plan view of an intraocular lens made in accordance with the present invention which has a far vision zone and a near vision zone defined by dividing the lens into quadrants.

Referring now to FIGS. 5-6, intraocular lenses 200 made in accordance with the present invention are shown. The lenses 200 have haptics 210 for holding the lens in place. As shown, each lens has near vision N and far vision F zones. In accordance with one aspect of the present invention, either the near of the far zone may comprise a high efficiency diffractive element while the other zone comprises a refractive element of the basic lens. Alternatively, as discussed with reference to FIG. 4, in certain embodiments of the present invention, both the near and far zones will comprise diffractive elements, each respectively of a different diffractive power.

The lenses depicted in FIGS. 5-6 also illustrate further variations of the geometries of the zones of different focal lengths created on the basic lens. As shown in FIGS. 2-4, it will be desirable in certain instances to create one or more circular or annular diffractive zones. As shown in FIGS. 5-6, it is also possible to divide the lens diametrically in halves or quarters, alternating the near and far vision zones accordingly. As will be readily understood by those of ordinary skill, the same zone layouts depicted in FIGS. 2-6 may be applied to contact lenses and other forms of lenses and are not limited to intraocular lenses.

Figure 7:
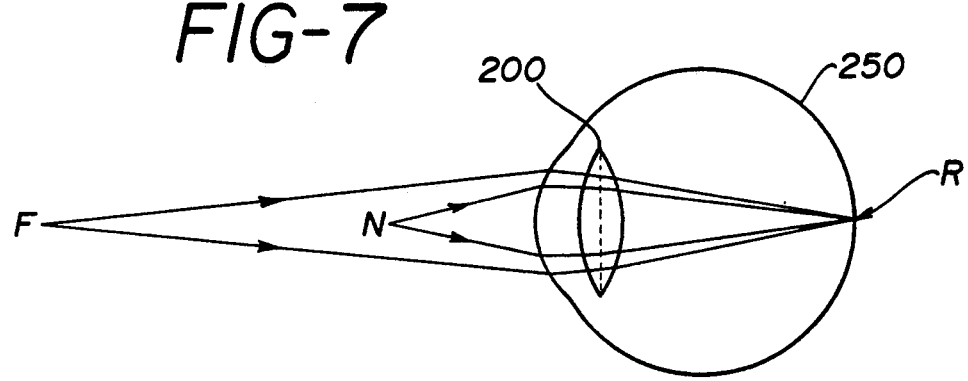
FIG. 7 is a schematic representation of the passage of light through a bi-focal intraocular lens made in accordance with the present invention.

The operation of an intraocular lens 200 within the eye 250 is shown in FIG. 7. Light from a near object N is focused on the retina R by the near vision zone. Light from a far object F is focused on the retina R by the far vision zone of the lens. Therefore, all of the light both the near and far objects is focused by the near or far zone respectively, resulting in a nearly 100% efficient lens.

Figure 8:
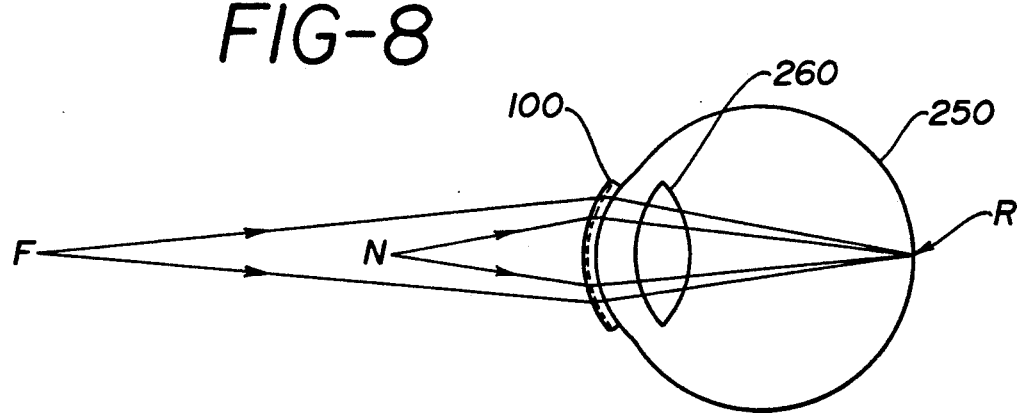
FIG. 8 is a schematic representation of the passage of light through a bi-focal contact lens made in accordance with the present invention.

Similarly, FIG. 8 depicts a contact lens 100 made in accordance with the present invention disposed on the cornea of an eye 250. Unlike the example of FIG. 7, the patient wearing a corrective contact lens also has a natural crystalline lens 260 within the eye.

As will be understood by those of ordinary skill the lenses discussed above may have a basic refractive power provided by the shape of the lens. The present invention may be applied to bi-convex or plano convex lenses, as well as to meniscus lenses, such as contact lenses.

Although certain embodiments of the present invention have be set forth in detail, these examples are not meant to be limiting. Numerous other embodiments and variations to the embodiments set forth will immediately present themselves to those of ordinary skill. Accordingly, reference should be made to the appended claims in order to determine the scope of the present invention.

What is claimed is:

1. A multifocal lens for correcting vision comprising:
 a basic lens element having a basic lens power and a basic focal length;
 one or more diffractive elements covering one or more zones of said basic lens element arranged as alternate semi-circular area and having a diffractive power,
 whereby a portion of the light travelling through said lens is focused at said basic focal length by said basic lens power, and another portion of the light travelling through said lens is focused t a different focal length by the combined power of said basic lens element and said diffractive elements.

2. A multifocal lens for correcting vision comprising:
 a basic lens element having a basic lens power and a basic focal length; and
 one of more diffractive elements covering one or more zones of said basic lens element arrayed as alternate quarter circular areas and having a diffractive power,
 whereby a portion of the light travelling through said lens is focused at said basic focal length by said basic lens power, and another portion of the light travelling through said lens is focused at a different focal length by the combined power of said basic lens element and said diffractive elements.

3. A multifocal lens for correcting vision comprising:
 a basic lens element having a basic lens power and a basic focal length;

one or more first diffractive elements covering one or more zones of said basic lens element and having a first diffractive power; and one or more second diffractive elements covering one or more zones of said basic lens element arranged as alternate semi-circular areas and having a second diffractive power, whereby a first portion of the light travelling through said lens is focused at a first focal length by the combined power of said basic lens element and said first diffractive elements, and another portion of the light travelling through said lens is focused at a second focal length by the combined power of said basic lens element and said second diffractive elements.

4. A multifocal lens for correcting vision comprising:

a basic lens element having a basic lens power and a basic focal length;

one or more first diffractive elements covering one or more zones of said basic lens element and having a first diffractive power; and one or more second diffractive elements covering one or more zones of said basic lens element arrayed as alternating quarter circular area and having a second diffractive power, whereby a first portion of the light travelling through said lens is focused at a first focal length by the combined power of said basic lens element and said first diffractive elements, and another portion of the light travelling through said lens is focused at a second focal length by the combined power of said basic lens element and said second diffractive elements.

* * * * *